(12) United States Patent
Kobayashi

(10) Patent No.: US 9,116,085 B2
(45) Date of Patent: Aug. 25, 2015

(54) MIST TESTING DEVICE

(75) Inventor: Tatsuo Kobayashi, Susono (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 137 days.

(21) Appl. No.: 14/003,979

(22) PCT Filed: Mar. 30, 2011

(86) PCT No.: PCT/JP2011/058011
§ 371 (c)(1),
(2), (4) Date: Sep. 9, 2013

(87) PCT Pub. No.: WO2012/131935
PCT Pub. Date: Oct. 4, 2012

(65) Prior Publication Data
US 2014/0007661 A1  Jan. 9, 2014

(51) Int. Cl.
G01N 1/28 (2006.01)
G01N 1/42 (2006.01)
G01N 15/02 (2006.01)

(52) U.S. Cl.
CPC .. G01N 1/28 (2013.01); G01N 1/42 (2013.01); G01N 15/0227 (2013.01)

(58) Field of Classification Search
CPC ........ G01N 1/42; G01N 1/28; G01N 15/0227
USPC ........................................ 73/64.56, 863, 864
See application file for complete search history.

(56) References Cited

U.S. PATENT DOCUMENTS

| 5,316,579 A * | 5/1994 | McMillan et al. ............... 118/50 |
| 2005/0028787 A1* | 2/2005 | Abrams et al. ................ 123/434 |
| 2011/0192047 A1 | 8/2011 | Itou et al. |
| 2012/0277617 A1 | 11/2012 | Eichler |

FOREIGN PATENT DOCUMENTS

| DE | 102007060701 A1 | 6/2008 |
| DE | 202009013577 U1 | 3/2010 |
| JP | S62273431 A | 11/1987 |
| JP | 62-279835 A | 12/1987 |
| JP | 01-036055 B2 | 7/1989 |
| JP | 11-352021 A | 12/1999 |
| WO | 2010/005021 A1 | 1/2010 |

OTHER PUBLICATIONS

Communication dated Oct. 28, 2014, issued by the State Intellectual Property Office of the People's Republic of China in counterpart Application No. 201180069874.7.

* cited by examiner

Primary Examiner — Hezron E Williams
Assistant Examiner — Marrit Eyassu
(74) Attorney, Agent, or Firm — Sughrue Mion, PLLC

(57) ABSTRACT

The present invention is a mist testing device having a freezing chamber 30 (a mist-freeze unit) that freezes a mist particle injected from a injection valve 12, a tray 40 (a frozen-mist-hold unit) that holds a frozen mist particle 42 frozen by the freezing chamber 30, and an analyze unit 86 that analyzes the frozen mist particle 42 held by the tray 40.

16 Claims, 10 Drawing Sheets

MIST TESTING DEVICE

CROSS REFERENCE TO RELATED APPLICATIONS

This is a National Stage of International Application No. PCT/JP2011/058011, filed Mar. 30, 2011, the contents of all of which are incorporated herein by reference in their entirety.

TECHNICAL FIELD

The present invention relates to a mist testing device.

BACKGROUND ART

A shape of a mist injected by an injection valve, a particle size of the mist and so on are important in an engine, in view of an unburnt fuel or a delay of vaporizing. Therefore, a mist from an injection valve is tested in a mass production line. There are various methods for the testing of a mist. For example, there are methods of measuring a particle size of a mist particle by optically taking an image of a mist such as an optical diffraction, a PDPA (Phase Doppler Particle Analyzer), a patternator, a laser holography, a laser shadow or the like. There is a method of testing a mist by radiating a light and using a scattered light. For example, Patent Document 1 discloses a method of measuring the number of micro particles with use of an intensity of the scattered light.

PRIOR ART DOCUMENTS

Patent Document 1: Japanese Published Examined Application No. 1-36055

SUMMARY OF THE INVENTION

Problems to be Solved by the Invention

However, in the method of measuring a particle size of a mist particle by optically taking an image of a mist as in the case of the above-mentioned mist testing method, there is a problem that a measuring of whole mist is difficult and a measuring accuracy with respect to a mist particle of extremely small particle and a mist particle not focused during taking an image is insufficient.

In view of the problem described above, it is an object of the present invention to provide a mist testing device that is capable of analyzing a mist with high accuracy.

Means for Solving the Problems

A mist testing device that tests a mist of a fuel injected by an injection valve used for an engine in accordance with the present invention includes: a mist-freeze unit that freezes a mist particle of the fuel injected from the injection valve; a frozen-mist-hold unit that holds the frozen mist particle frozen by the mist-freeze unit; an analyze unit that analyzes the frozen mist particle held by the frozen-mist-hold unit. With the mist testing device in accordance with the present invention, a mist particle is frozen and hardened and becomes a frozen mist particle. Thereby, the mist particle can keep a mist shape. Therefore, it is possible to analyze a mist with high accuracy by analyzing the frozen mist particle.

In the above structure, the analyze unit may analyze the frozen mist particle by taking an image of the frozen mist particle held by the frozen-mist-hold unit. In the above-mentioned structure, an image of the frozen mist particle held by the frozen-mist-hold unit may be taken with two or more different focal lengths. With the structures, it is possible to analyze the frozen mist particles having a different particle size.

In the above-mentioned structure, the analyze unit may analyze the frozen mist particle by measuring a surface roughness of the frozen-mist-hold unit holding the frozen mist particle. With the structure, a surface of the frozen-mist-hold unit is a measure reference. And it is possible to analyze the frozen mist particle with high accuracy and a short time.

In the above-mentioned structure, a plurality of the frozen-mist-hold units of which mesh has a different roughness may be provided, and the analyze unit may analyze the frozen mist particle by measuring a mass of the frozen mist particle held by each of the plurality of the frozen-mist-hold units.

In the above-mentioned structure, an injection chamber that splits and diffuses a mist injected by the injection valve, a freezing chamber, of which temperature is kept low so that the split and diffused mist particle is frozen, that is communicated with the injection chamber and has the frozen-mist-hold unit, and a shutter that switches a communication and non-communication between the injection chamber and the freezing chamber may be provided. With the structure, it is possible to keep the temperature of the freezing chamber at low temperature for freezing the mist particle and suppress cooling of the injection chamber for splitting and diffusing the mist.

In the above-mentioned structure, a shutter control unit that closes the shutter after the injecting of the mist by the injection valve is finished may be provided.

In the above-mentioned structure, a temperature measure unit that measures a temperature in the freezing chamber and a coolant gas control unit that controls an amount of a coolant gas guided into the freezing chamber so that the temperature measured by the temperature measure unit is a predetermined temperature may be provided. With the structure, the temperature in the freezing chamber can be kept at a predetermined temperature. It is therefore possible to freeze the mist particle more accurately.

In the above-mentioned structure, the freezing chamber may have a circular cylinder shape, and a coolant gas guide pipe that introduces a coolant gas into the freezing chamber from an oblique direction with respect to a side wall of the freezing chamber having a circular cylinder may be connected to the freezing chamber. With the structure, it is possible to stir the coolant gas in the freezing chamber. Therefore, it is possible to equalize the temperature in the freezing chamber and freeze the mist particle evenly.

In the above-mentioned structure, the freezing chamber and the shutter may be made of a member having a thermal conductivity lower than that of a member structuring the injection chamber. With the structure, it is suppressed that the temperature in the freezing chamber increases because of an outer temperature or the temperature in the injection chamber.

In the above-mentioned structure, a stirring unit may be provided in the freezing chamber. With the structure, it is possible to equalize the temperature in the freezing chamber and freeze the mist particle evenly.

In the above-mentioned structure, a frozen mist collect unit that collects the frozen mist particle from the frozen-mist-hold unit after the analyzing by the analyze unit may be provided. With the structure, it is possible to collect the frozen mist particle before vaporizing and reduce an amount of fuel remained in the freezing chamber.

In the above-mentioned structure, the frozen mist collect unit may incline the frozen-mist-hold unit, drops a frozen mist particle held by the frozen-mist-hold unit from the frozen-mist-hold unit, and collects the frozen mist particle. With the structure, it is possible to collect the frozen mist particle speedily.

In the above-mentioned structure, the frozen mist collect unit may collect the frozen mist particle by unfreezing a frozen mist particle held by the frozen-mist-hold unit. With the structure, it is possible to collect the frozen mist particle speedily.

In the above-mentioned structure, the frozen mist particle may be collected to a collect tray via an exhaust path. With the structure, it is possible to use the fuel again.

In the above-mentioned structure, the frozen-mist-hold unit may have micro projections provided at an interval of 0.1 µm or less, and the frozen mist particle may be held on the micro projections. With the structure, a contact area between the frozen mist particle and the frozen-mist-hold unit is reduced. And adfreezing of the frozen mist particle on the frozen-mist-hold unit can be suppressed because of a thermal insulating layer of air, even if the frozen mist particle is a particle having a small thermal capacity.

In the above-mentioned structure, an image unit that takes an image of a mist being injected by the injection valve may be provided. With the structure, a mist image can be taken. Therefore, a shape of the mist can be clarified.

Effects of the Invention

According to the present invention, it is possible to remain a shape of a mist by freezing and hardening a mist particle into a frozen mist particle and analyze the mist particle with high accuracy.

MODES FOR CARRYING OUT THE INVENTION

Embodiments for carrying out the present invention are now described with reference to the drawings.

Embodiment 1

Figure 1:
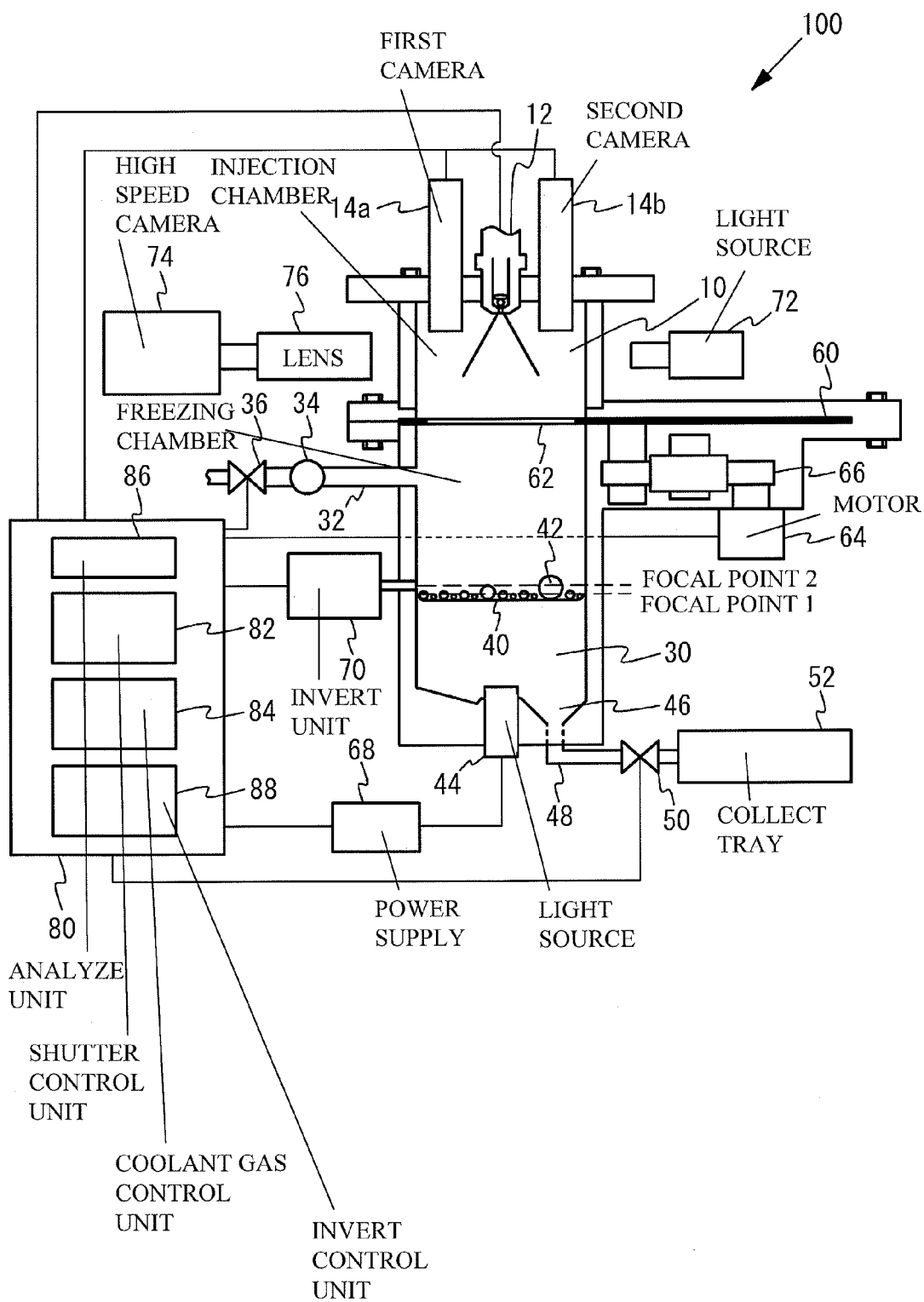
FIG. 1 illustrates an example of a side view of an overall structure of a mist testing device in accordance with an embodiment 1.
Figure 2:
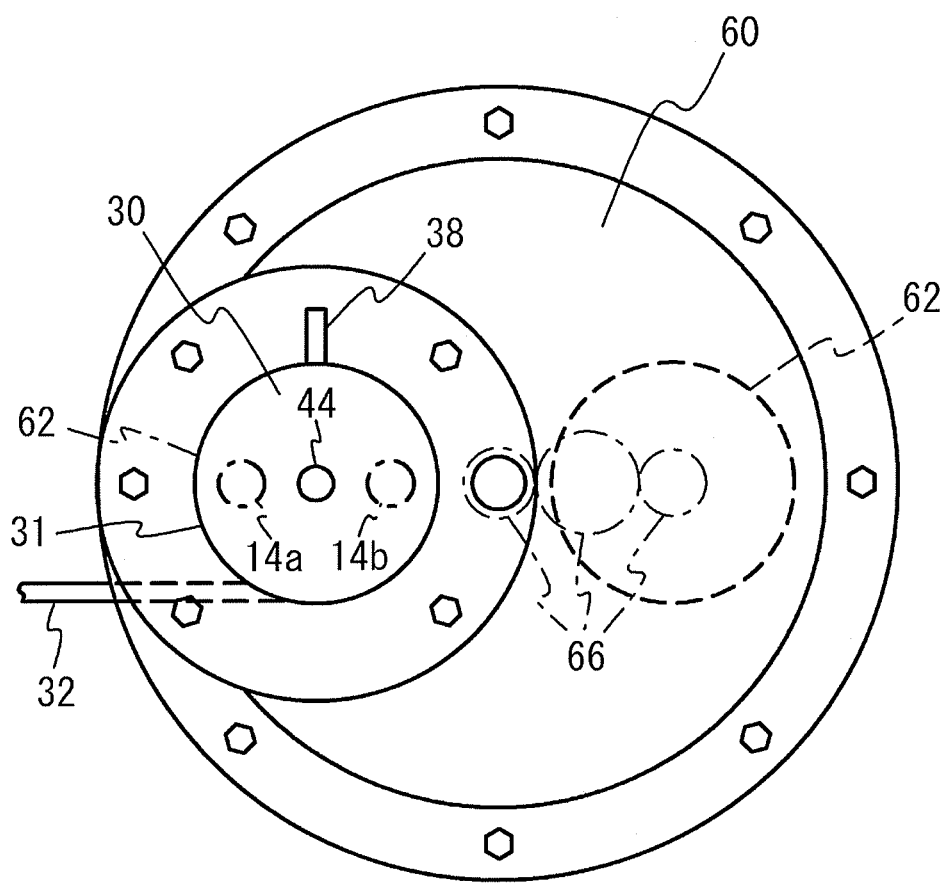
FIG. 2 illustrates an example of a plane view of the mist testing device in accordance with the embodiment 1.

FIG. 1 illustrates an example of a side view of an overall structure of a mist testing device in accordance with an embodiment 1. FIG. 2 illustrates an example of a plane view of the mist testing device in accordance with the embodiment 1. With reference to FIG. 1 and FIG. 2, the mist testing device 100 has a room-temperature injection chamber 10, a freezing chamber 30 cooled to an extremely low temperature of −100 degrees C. or less, and a control unit 80. The injection chamber 10 and the freezing chamber 30 have a circular cylinder shape and are communicated with each other. A shutter 60 for switching a communication and a non-communication between the injection chamber 10 and the freezing chamber 30 is provided between the injection chamber 10 and the freezing chamber 30. The freezing chamber 30 and the shutter 60 are structured with a low thermal conductivity member such as a ceramics. The shutter 60 has a disk shape and has two windows 62 that are located symmetrically with respect to a center point of the shutter 60. When a motor 64 drives a gear wheel 66 and the gear wheel 66 rotates, the shutter 60 rotates. The driving of the motor 64 rotating the shutter 60 is controlled by the control unit 80. That is, the control unit 80 acts as a shutter control unit 82 for controlling the rotation of the shutter 60.

When one of the two windows 62 is positioned between the injection chamber 10 and the freezing chamber 30 (a condition of FIG. 1 and FIG. 2), the shutter 60 is opened and the injection chamber 10 is communicated with the freezing chamber 30. When the shutter 60 rotates by 90 degrees from the condition, the shutter 60 is inserted between the injection chamber 10 and the freezing chamber 30 and the shutter 60 is closed. Thus, the injection chamber 10 is not communicated with the freezing chamber 30. When the shutter 60 further rotates by 90 degrees, the other of the two windows 62 is inserted between the injection chamber 10 and the freezing chamber 30 and the shutter 60 is opened. Thus, the injection chamber 10 is communicated with the freezing chamber 30.

A injection valve 12 is mounted at a center portion of an upper portion of the injection chamber 10. For example, the injection valve 12 makes a mist from a fuel and injects the mist in accordance with an instruction from the control unit 80. A diameter of a mist particle injected by the injection valve 12 is, for example, 1 vim to 10 µm. The mist injected by the injection valve 12 is split and diffused in the injection chamber 10. A side wall of the injection chamber 10 is made of a glass or the like and is transparent. A light source 72 is provided out of one of side walls of the injection chamber 10. A high speed camera 74 having a frame speed of 10 thousands to 500 thousands is provided out of the other of the side walls of the injection chamber 10 and face with the light source 72. The high speed camera 74 takes a mist image of a mist injected by the injection valve 12. A lens 76 is used for focusing a mist that is an objective of the high speed camera 74.

At the upper portion of the injection chamber 10, a first camera 14a and a second camera 14b are further mounted on both sides of the injection valve 12. A focusing length of the first camera 14a is different from that of the second camera 14b. For example, the focusing length of the first camera 14a is longer than that of the second camera 14b. Imaging of the first camera 14a and the second camera 14b will be described later.

A coolant gas guide pipe 32 is connected to the freezing chamber 30. For example, liquid nitrogen is introduced into the freezing chamber 30 from the coolant gas guide pipe 32 as a coolant gas. Thus, a temperature of the freezing chamber 30 is kept at an extremely low temperature of −100 degrees C. or less. The coolant gas guide pipe 32 is connected to a side wall 31 of the freezing chamber 30 having a circular cylinder shape from an oblique direction. The coolant gas guide pipe 32 has a pressure indicator 34 and a flow regulate valve 36. An opening and closing of the flow regulate valve 36 is controlled by the control unit 80. A temperature sensor 38 is mounted on the side wall 31 of the freezing chamber 30. The control unit 80 controls the flow regulate valve 36 in accordance with a temperature in the freezing chamber 30 measured by the temperature sensor 38, and adjusts a flow rate of liquid nitrogen flowing into the freezing chamber 30. That is, the control unit 80 acts as a coolant gas control unit 84 for controlling the flow rate of the coolant gas flowing into the freezing chamber 30. For example, the control unit 80 adjusts an amount of the coolant gas flowing into the freezing chamber 30 so that a temperature in the freezing chamber 30 is maintained at a predetermined temperature.

A transparent tray 40 is provided in the freezing chamber 30. When a mist particle injected by the injection valve 12 reaches the freezing chamber 30, the mist particle is frozen and becomes a frozen mist particle 42. The tray 40 holds the frozen mist particle 42. A light source 44 is mounted on a lower portion of the freezing chamber 30. The light source 44 emits a light when the control unit 80 controls a power supply 68. The first camera 14a and the second camera 14b take an image of the frozen mist particle 42 illuminated by the light source 44, in accordance with an instruction of the control unit 80. The control unit 80 analyzes the frozen mist particle 42 from the images of the frozen mist particle 42 taken by the first camera 14 and the second camera 14*b*. For example, an average particle size, a particle size distribution, a mass distribution or the like of the frozen mist particle 42 is analyzed. That is, the control unit 80 acts as an analyze unit 86 for analyzing the frozen mist particle 42. There are a frozen mist particle having a large particle size and a frozen mist particle having a small particle size in the frozen mist particles 42 held by the tray 40. The first camera 14*a* having a large focusing length (a focal point 1) photographically takes an image of the frozen mist particle 42 having a small particle size. The second camera 14*b* having a small focusing length (a focal point 2) photographically takes an image of the frozen mist particle 42 having a large particle size.

An invert unit 70 for turning the tray 40 upside down is provided and is controlled by the control unit 80. The control unit 80 turns the tray 40 upside down with use of the invert unit 70 after the first camera 14*a* and the second camera 14*b* take an image of the frozen mist particle 42 held by the tray 40. Thus, the frozen mist particle held by the tray 40 drops on a bottom of the freezing chamber 30. That is, the control unit 80 has an invert control unit 88 for turning the tray 40 upside down after taking an image of the frozen mist particle 42.

A concave portion 46 is formed on the bottom of the freezing chamber 30. An exhaust pipe 48 is connected to the bottom of the concave portion 46. The frozen mist particle 42 dropped from the tray 40 is guided to the exhaust pipe 48. The exhaust pipe 48 has a valve 50 that is an electromagnetic valve controlled by the control unit 80. When the valve 50 is opened, the frozen mist particle 42 is collected by a collect tray 52 connected to the exhaust pipe 48.

A description is now given of an analyzing method of the frozen mist particle 42 held by the tray 40. FIG. 3 illustrates an example of a flow chart of the analyzing method of the frozen mist particle 42. With reference to FIG. 3, the control unit 80 drives the motor 64 and rotates the shutter 60 by 90 degrees just before or just after the injecting of the injection valve 12, and opens the shutter 60 (Step S10). Thus, the injection chamber 10 is communicated with the freezing chamber 30. A mist particle injected by the injection valve 12 reaches the freezing chamber 30, is frozen in the freezing chamber 30 and becomes the frozen mist particle 42. The frozen mist particle 42 is held by the tray 40 provided in the freezing chamber 30.

Next, the control unit 80 drives the motor 64, rotates the shutter 60 by 90 degrees and closes the shutter 60 after a first predetermined time passes after the injection valve 12 finishes the injecting (Step S12). The first predetermined time can be determined in view of a splitting time of a mist injected by the injection valve 12.

Next, the control unit 80 drives the motor 64, rotates the shutter 60 by 90 degrees and opens the shutter 60 after a second predetermined time passes after closing of the shutter 60 (Step S14). The second predetermined time can be determined in view of a freezing time of the mist particle and a time for stably depositing the frozen mist particle 42 on the tray 40.

Next, the control unit 80 maintains the opening of the shutter 60, makes the light source 44 emit a light, and takes images of the frozen mist particle 42 held by the tray 40 with use of the first camera 14*a* and the second camera 14*b* (Step S16). After taking the images, the control unit 80 drives the motor 64, rotates the shutter 60 by 90 degrees, and closes the shutter 60 (Step S18). Next, the control unit 80 analyzes the frozen mist particles 42 from the images of the frozen mist particle 42 taken by the first camera 14*a* and the second camera 14*b* (Step S20). For example, an average particle size, a particle distribution, a mass distribution or the like of the frozen mist particle 42 is obtained.

As mentioned above, in accordance with the embodiment 1, the freezing chamber 30 (a mist-freeze unit) for freezing a mist particle injected by the injection valve 12, the tray 40 (a frozen-mist-hold unit) for holding the frozen mist particle 42, the analyze unit 86 for analyzing the frozen mist particle 42 by taking images of the frozen mist particle 42 held by the tray 40 with use of the first camera 14*a* and the second camera 14*b* are provided. The analyze unit 86 analyzes the frozen mist particle 42 from the taken images, and obtains an average particle size, a particle distribution, a mass distribution or the like of the frozen mist particle 42. Thus, the mist particle injected by the injection valve 12 is frozen and hardened and becomes the frozen mist particle 42. Thereby, the mist particle can keep a mist shape for a long time. Therefore, it is possible to analyze a mist with high accuracy by taking an image of the frozen mist particle 42 and analyzing the frozen mist particle 42 from the taken image.

In the embodiment 1, as an example, the frozen mist particles 42 are analyzed by taking images of the frozen mist particles 42 with use of the first camera 14*a* and the second camera 14*b* having a different focusing length. The particle size of the frozen mist particles 42 held by the tray 40 is various from extremely small to extremely large. It is therefore possible to take images of the frozen mist particles 42 in a range from extremely small to extremely large by taking images of the frozen mist particles with use of the first camera 14*a* and the second camera 14*b* having a different focusing length. That is, it is possible to analyze the frozen mist particles 42 having a different particle size. In this way, it is preferable to take images of the frozen mist particles 42 held by the tray 40 with two or more focusing lengths. A single camera capable of selecting a plurality of focusing lengths may be provided instead of mounting a plurality of cameras having a different focusing length such as the embodiment 1.

A single camera not capable of switching a focal length may be mounted, and the camera may take an image of the frozen mist particles 42 held by the tray 40. The structure is not limited to the case where the light source 44 is mounted on the bottom of the freezing chamber 30, the frozen mist particle 42 is illuminated from the lower side of the tray 40, and an image of the frozen mist particle 42 is taken, as illustrated in FIG. 1. The light source 44 may be mounted on the upper portion of the injection chamber 10, the frozen mist particle 42 may be illuminated from the upper side of the tray 40, and an image of the frozen mist particle 42 may be taken. In this case, the tray 40 may not be transparent.

As illustrated in FIG. 1, the injection chamber 10 for splitting and diffusing a mist injected by the injection valve 12, the freezing chamber 30, of which temperature is kept low for freezing the mist particle split and diffused in the injection chamber 10, being communicated with the injection chamber 10 and having the tray 40, and the shutter 60 switching communication and non-communication between the injection chamber 10 and the freezing chamber 30 are provided. Thus, it is possible to keep the temperature of the freezing chamber 30 for freezing a mist particle low and suppress cooling of the injection chamber 10 for splitting and diffusing a mist.

Figure 3:
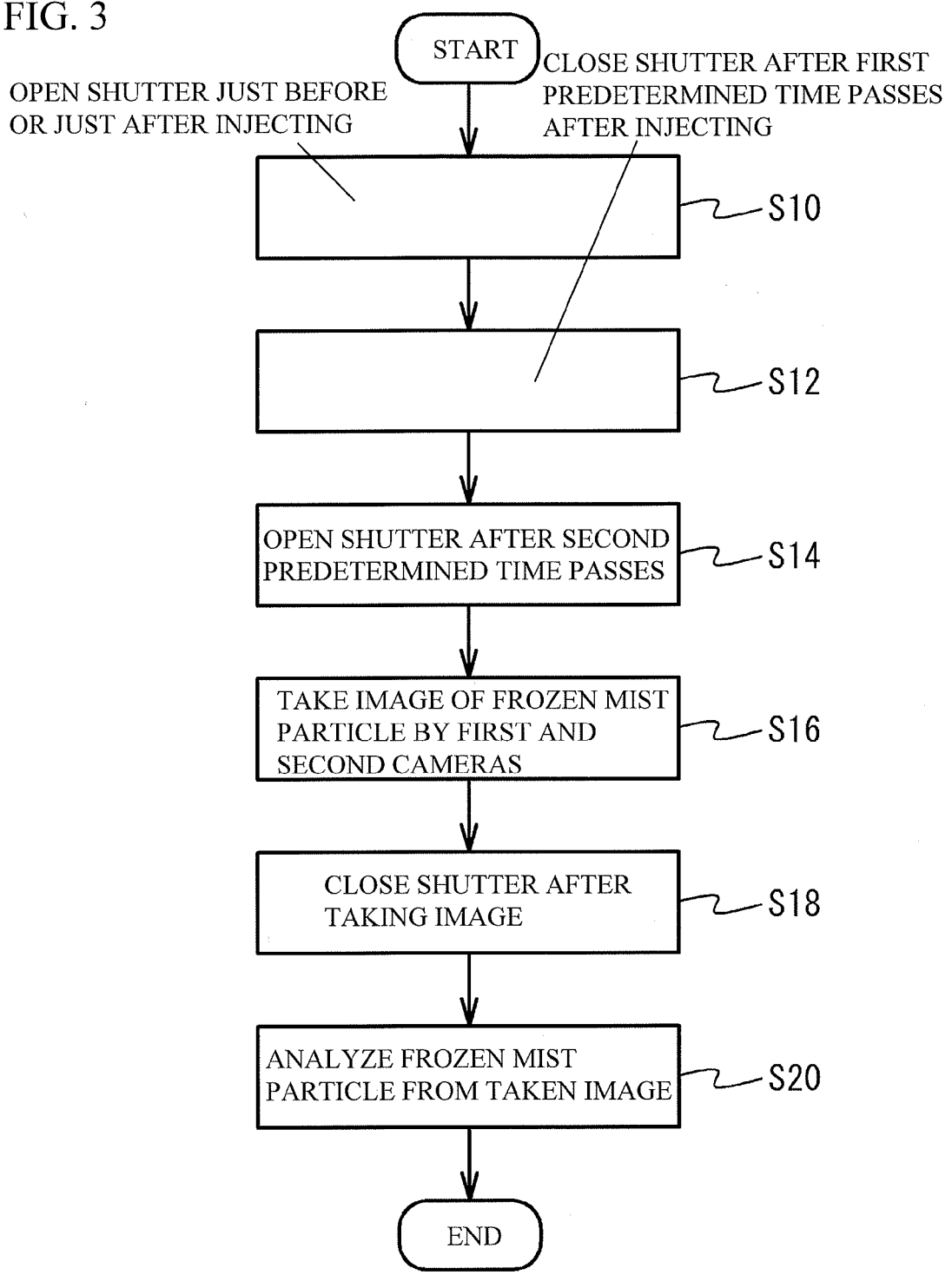
FIG. 3 illustrates an example of a flow chart of an analyzing method of a frozen mist particle.

In view of keeping the temperature of the freezing chamber 30 low and suppressing the cooling of the injection chamber 10, the control of the shutter 60 as illustrated in FIG. 3 is preferable. That is, it is preferable that the shutter 60 is opened just before or just after the starting of injecting of the mist from the injection valve 12, the shutter 60 is closed after the first predetermined time passes after the injecting is finished, the shutter 60 is opened again after the second predetermined time passes, and the shutter 60 is closed after taking images. It is preferable that the first predetermined time and the second predetermined time can be optionally changed by a user.

It is preferable that the temperature sensor 38 for measuring the temperature in the freezing chamber 30 is provided, and an amount of the coolant gas guided into the freezing chamber 30 is controlled so that the temperature measured by the temperature sensor 38 becomes a predetermined temperature. With the structure, the temperature in the freezing chamber 30 can be kept at a predetermined temperature. Therefore, it is possible to freeze a mist particle injected by the injection valve 12 more accurately.

It is preferable that the freezing chamber 30 has a circular cylinder shape, and the coolant gas guide pipe 32 for guiding the coolant gas into the freezing chamber 30 is connected to the side wall 31 of the freezing chamber 30 having the circular cylinder shape from an oblique direction. With the structure, it is possible to swivel the coolant gas in the freezing chamber 30. Therefore, the temperature in the freezing chamber 30 can be equalized, and mist particles injected by the injection valve 12 can be frozen evenly. It is preferable that the coolant gas guide pipe 32 is connected to the side wall 31 of the freezing chamber 30 from a tangential direction. This is because the coolant gas can be swiveled in the freezing chamber 30 effectively.

It is preferable that the freezing chamber 30 and the shutter 60 are made of a member having a thermal conductivity lower than that of a member structuring the injection chamber 10. With the structure, it is suppressed that the temperature of the freezing chamber 30 increases because of an outer temperature or a temperature in the injection chamber 10.

It is preferable that the frozen mist particle 42 is collected from the tray 40 by turning the tray 40 upside down with use of the invert unit 70 and dropping the frozen mist particle 42 from the tray 40, after finishing the analyzing of the frozen mist particle 42. With the structure, the frozen mist particle 42 can be collected speedily. Therefore, the frozen mist particle 42 can be collected before a vaporizing of the frozen mist particle 42. And, an amount of a fuel remaining in the freezing chamber 30 can be reduced. A method of collecting the frozen mist particle 42 from the tray 40 is not limited to the case where the tray 40 is turned upside down and the frozen mist particle 42 is dropped from the tray 40. The frozen mist particle 42 may be collected by inclining the tray 40 and dropping the frozen mist particle 42 from the tray 40. The frozen mist particle 42 may be collected from the tray 40 after finishing the analyzing of the frozen mist particle 42 with another method.

Regarding the collecting of the frozen mist particle 42, it is preferable that the frozen mist particle 42 is collected into the collect tray 52 via the exhaust pipe 48. With the structure, the fuel can be used again. When the valve 50 is provided in the exhaust pipe 48, temperature increasing of the freezing chamber 30 can be suppressed. And, when the valve 50 is an electromagnetic valve, a cold injury of an operator because of an opening and closing of the valve 50 can be prevented.

Figure 4:
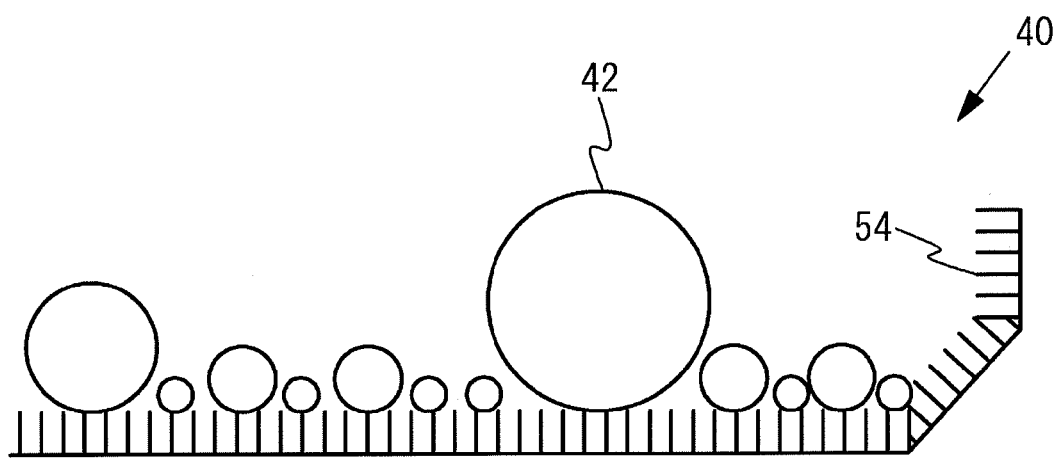
FIG. 4 illustrates an example of a side view of a tray.

FIG. 4 illustrates an example of a side view of the tray 40. It is preferable that micro projections 54 are provided on a surface of the tray 40 at an interval of 0.1 µm or less, and the frozen mist particles 42 are held by the micro projections 54. With the structure, a contact area between the frozen mist particle 42 and the tray 40 is reduced. And adfreezing of the frozen mist particle 42 on the tray 40 can be suppressed because of a thermal insulating layer of air, even if the frozen mist particle 42 is a particle of 1 µm or the like and has a small thermal capacity. The micro projection 54 may be formed by a chemical process with use of a machine processing and an agent. A hair of animals and plants may be used as the micro projection 54.

It is preferable that the light source 72 is provided out of one side wall of the injection chamber 10, the high speed camera 74 is provided out the other side wall of the injection chamber 10 facing the one side wall, and the high speed camera 74 takes a mist image of a mist being injected by the injection valve 12, as illustrated in FIG. 1. With the structure, it is possible to take a mist image during injecting. Therefore, a mist shape can be clarified.

Figure 5:
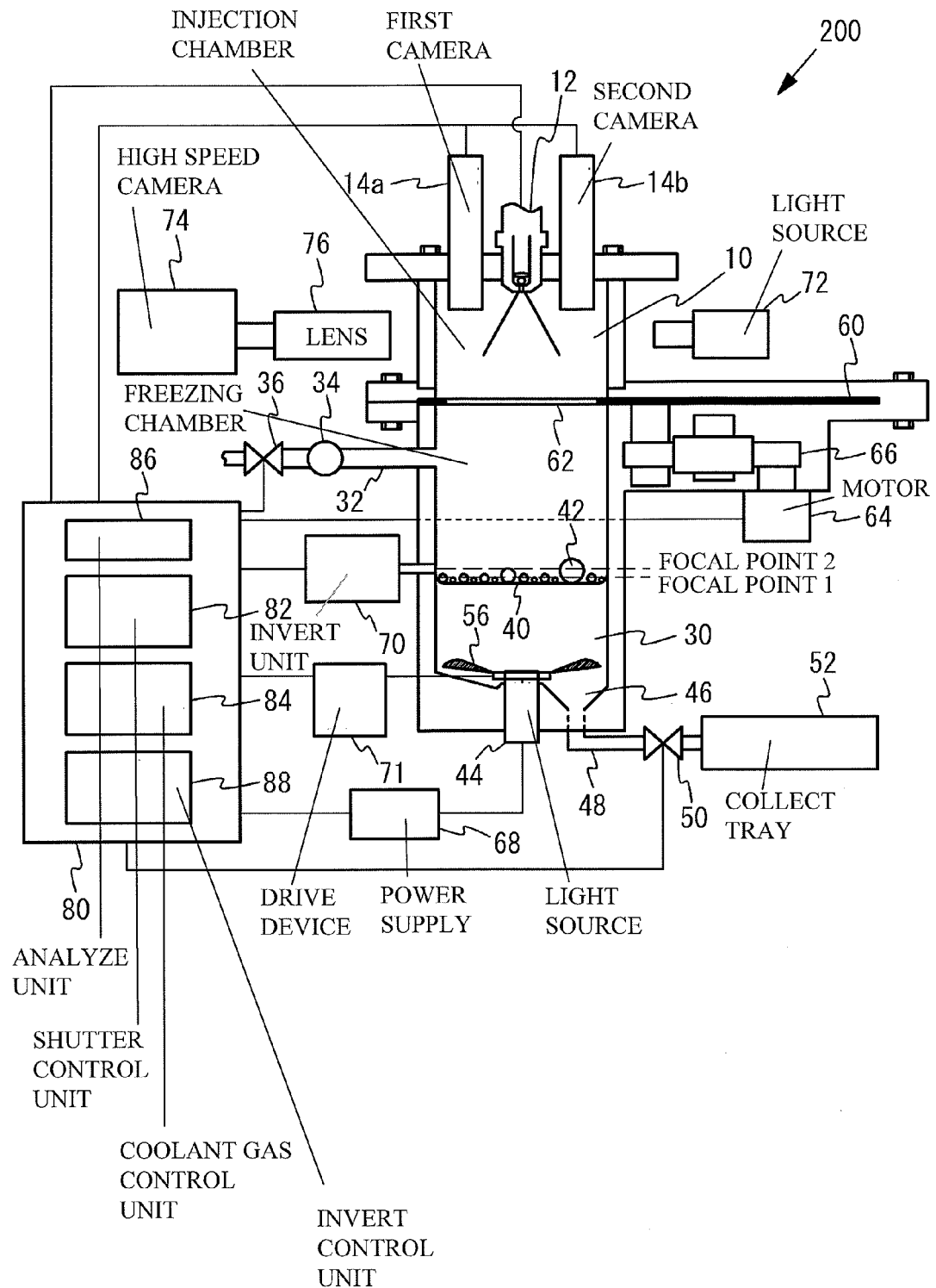
FIG. 5 illustrates an example of a side view of an overall structure of a mist testing device in accordance with a modified embodiment of the embodiment 1.

FIG. 5 illustrates an example of a side view of an overall structure of a mist testing device in accordance with a modified embodiment of the embodiment 1. With reference to FIG. 5, a mist testing device 200 has a stirring fan 56 for stirring air in the freezing chamber 30 on the bottom of the freezing chamber 30. The stirring fan 56 is driven by a drive device 71 controlled by the control unit 80. Other structures are the same as the embodiment 1 and are illustrated in FIG. 1 and FIG. 2. Therefore, an explanation of the other structures is omitted.

In accordance with the modified embodiment of the embodiment 1, the stirring fan 56 is provided in the freezing chamber 30. Thus, the temperature in the freezing chamber 30 can be equalized, when the stirring fan 56 is driven with the shutter 60 being closed. It is therefore possible to freeze mist particles injected by the injection valve 12 evenly. Instead of the stirring fan 56, another member may be used when the member is capable of stirring the air in the freezing chamber 30.

Embodiment 2

Figure 6:
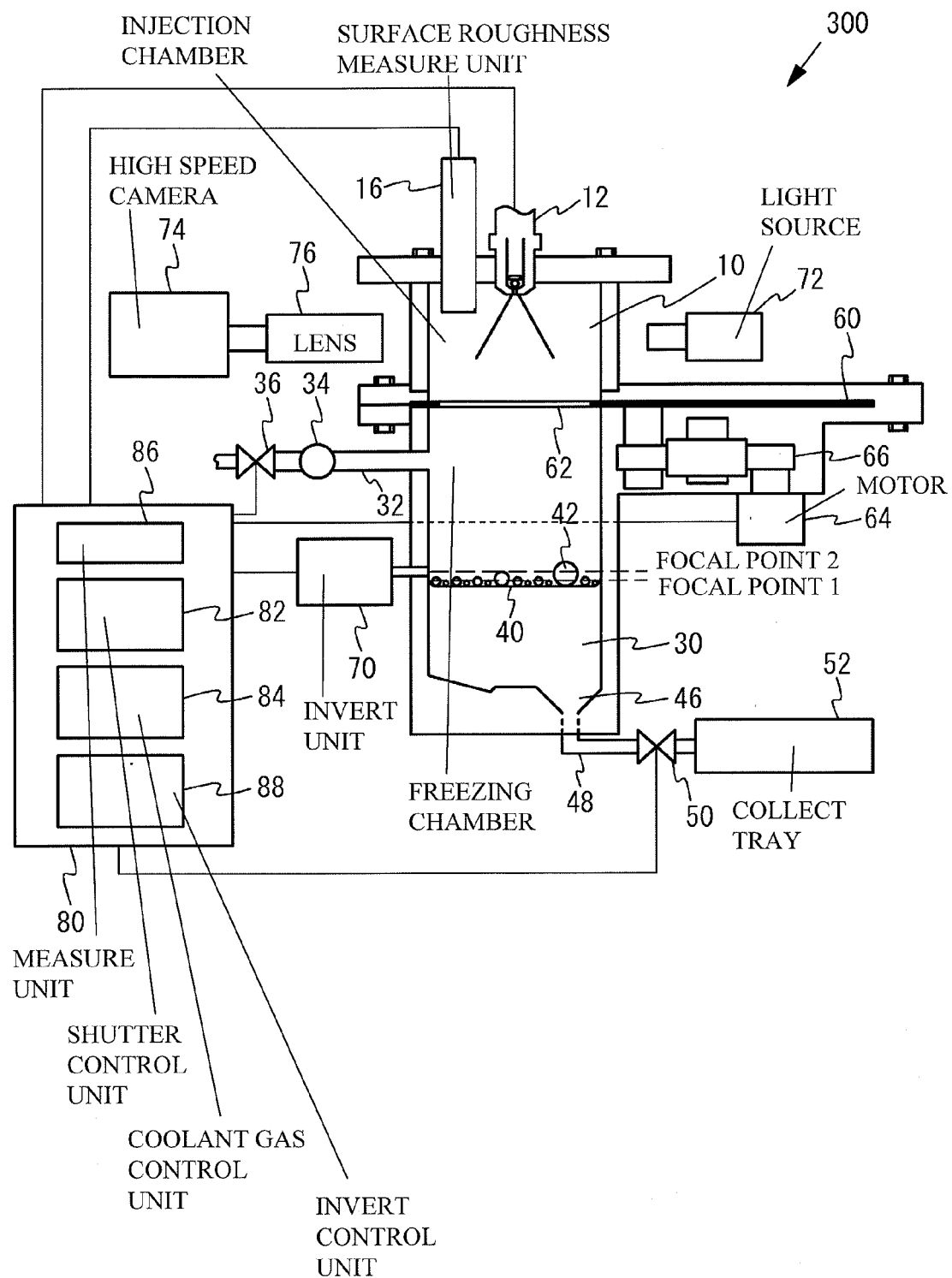
FIG. 6 illustrates a side view of an overall structure of a mist testing device in accordance with an embodiment 2.

FIG. 6 illustrates a side view of an overall structure of a mist testing device in accordance with an embodiment 2. With reference to FIG. 6, in a mist testing device 300, a surface roughness measure unit 16 is mounted on the upper portion of the injection chamber 10 instead of the first camera 14a and the second camera 14b. The light source 44 is not mounted on the bottom of the freezing chamber 30. Other structures are the same as the embodiment 1 and are illustrated in FIG. 1 and FIG. 2. Therefore, an explanation of the other structures is omitted.

The surface roughness measure unit 16 is, for example, a surface roughness measure unit of a light wave interference type and measures a surface roughness of the tray 40 by scanning a whole surface of the tray 40 holding the frozen mist particle 42 in accordance with an instruction of the control unit 80. And, the control unit 80 analyzes the frozen mist particle 42 from the surface roughness of the tray 40 measured by the surface roughness measure unit 16. For example, a particle size, the number of particles and so on of the frozen mist particle 42 are calculated.

The frozen mist particle 42 held by the tray 40 may be analyzed by measuring the overall surface roughness of the tray 40 holding the frozen mist particle 42 as in the case of the embodiment 2. In this case, the surface of the tray 40 is a measure reference of the surface roughness measure unit 16. And it is possible to analyze the frozen mist particle 42 with high accuracy and a short time.

Embodiment 3

Figure 7:
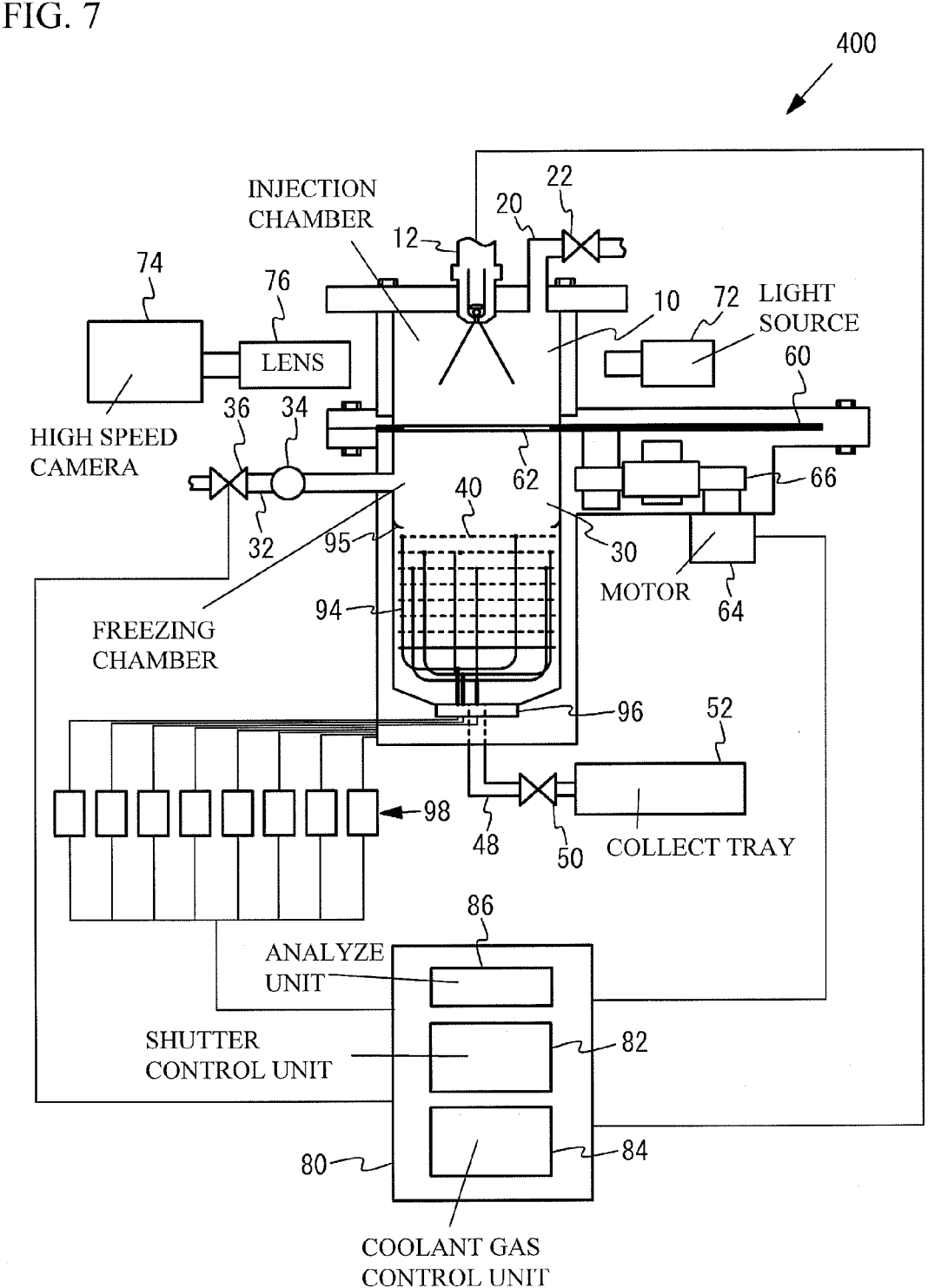
FIG. 7 illustrates an example of a side view of an overall structure of a mist testing device in accordance with an embodiment 3.
Figure 8:
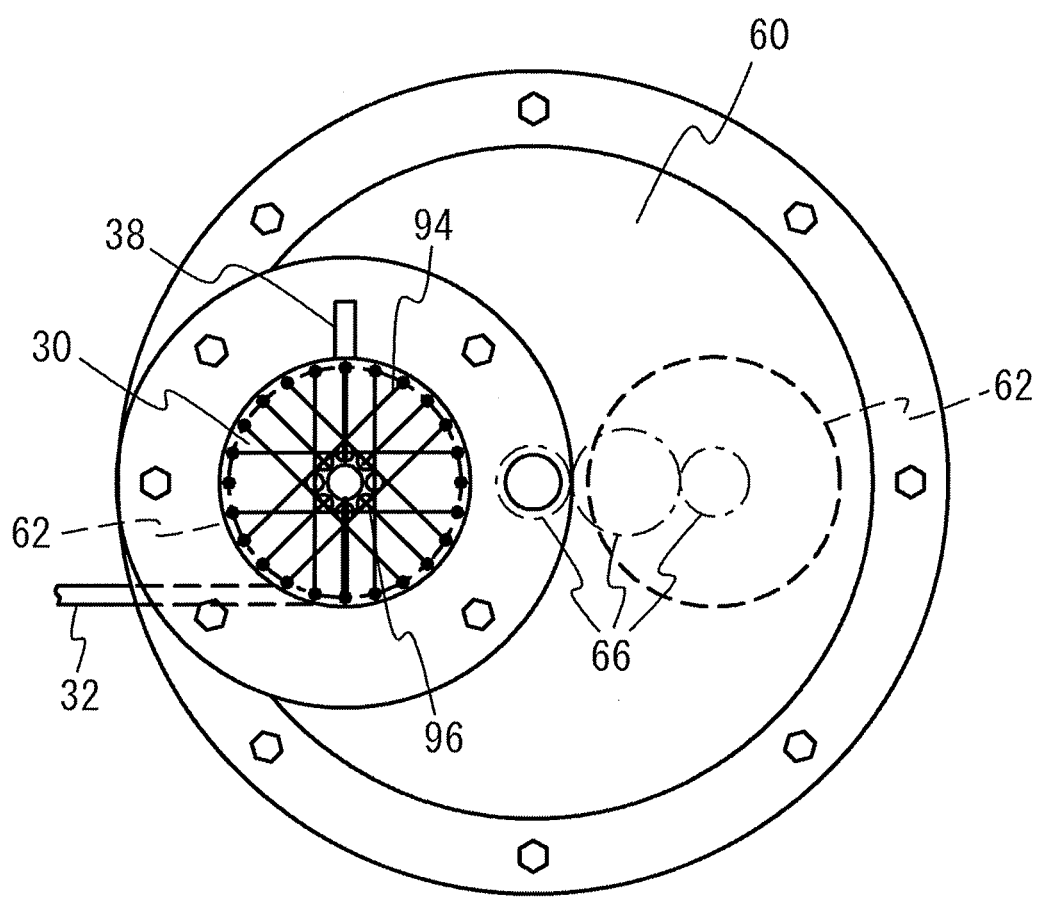
FIG. 8 illustrates an example of a plane view of a main structure of the mist testing device in accordance with the embodiment 3.

FIG. 7 illustrates an example of a side view of an overall structure of a mist testing device in accordance with an embodiment 3. FIG. 8 illustrates an example of a plane view of a main structure of the mist testing device in accordance with the embodiment 3. With reference to FIG. 7 and FIG. 8, the mist-resting device 400 has the injection chamber 10, the freezing chamber 30, the control unit 80 and the shutter 60. A warm air flow pipe 20 for flowing a warm air is connected to the upper portion of the injection chamber 10. The warm air flow pipe 20 has a valve 22. The first camera **14*a* and the second camera 14*b*** as in the case of the embodiment 1 are not provided.

For example, eight trays 40 are arranged in order at an interval in the freezing chamber 30 so that each of the trays 40 is overlapped with each other. One of the trays 40 located at the bottom has a plane shape. The others have a mesh shape. A mesh roughness of the trays 40 increases from the bottom to an upper stage. The mesh roughness of the trays 40 is measured in advance.

Mist particles injected by the injection valve 12 are frozen in the freezing chamber 30 and become frozen mist particles 42 having various particle sizes. The trays 40 have a function of holding the frozen mist particles 42. The frozen mist particle 42 having a large particle size is held by the tray 40 on the upper side, and the frozen mist particle having a small particle size is held by the tray 40 on the lower side, because the mesh roughness of the trays 40 increases from the bottom to the upper stage. The tray 40 located at the bottom holds the frozen mist particle 42 having an extremely small size and passing through the trays 40 having the mesh shape, because the tray 40 located at the bottom has the plane shape with no mesh shape. That is, each of the trays 40 holds the frozen mist particle 42 having a different particle size.

Figure 9:
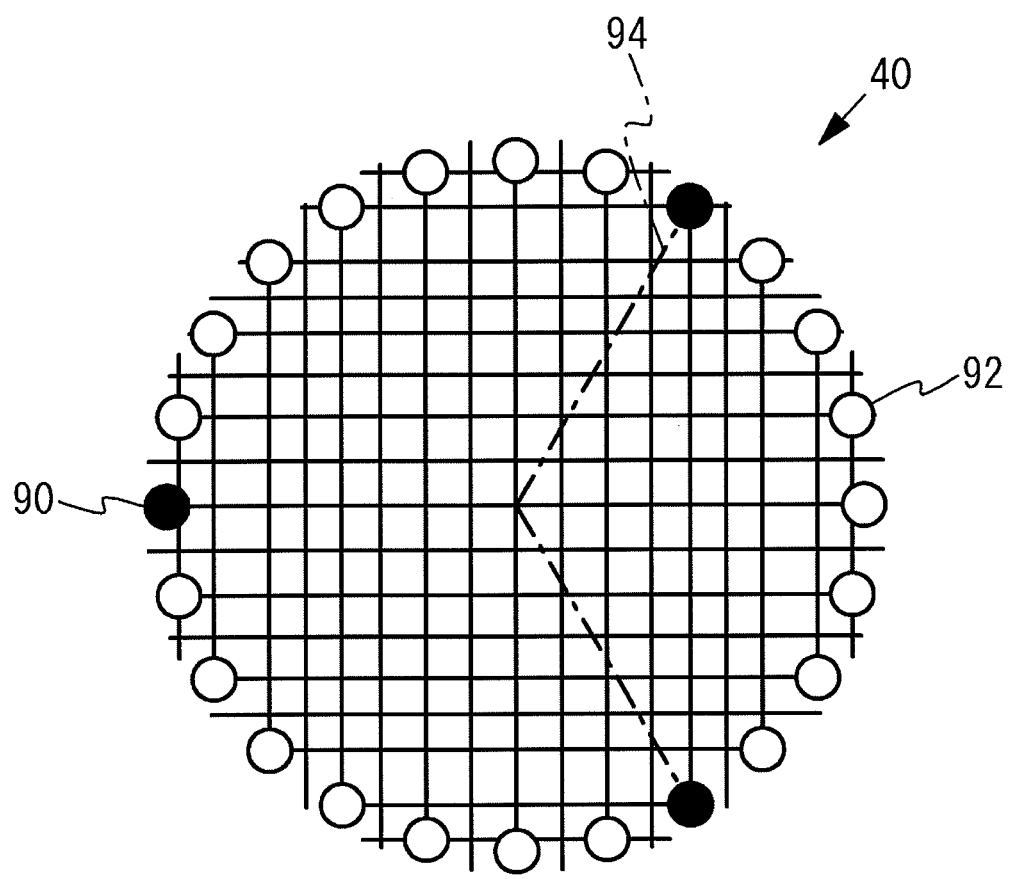
FIG. 9 illustrates a plane view of the tray.

FIG. 9 illustrates a plane view of the tray 40. In FIG. 9, the tray 40 having a mesh shape is illustrated as an example. With reference to FIG. 9, the tray 40 has a disc shape, and has concave portions 90 at every 120 degrees of a circumference and has through holes 92 at every 15 degrees of the circumference other than the concave portions 90.

With reference to FIG. 7 to FIG. 9, the tray 40 are stable supported by a support rod 94 at the three concave portions 90 formed at every 120 degrees. Another support rod 94 supporting another tray 40 passes through the through hole 92 formed at every 15 degrees. Thus, the support rod 94 does not interference with the through hole 92. Load sensors 96 are provided at the bottom of the freezing chamber 30. Three support rods 94 supporting the tray 40 are combined into a single member and are connected to one of the load sensors 96. The load sensors 96 are connected to a mass meter 98. Thus, it is possible to measure a mass of each of the trays 40.

The control unit 80 measures a mass of each of the trays 40 with the mass meter 98, and analyzes the frozen mist particle 42 by measuring the mass of the frozen mist particle 42 of each of the trays 40 having different particle size. For example, the control unit 80 calculates the number of particles from the mass of each particle size and obtains a particle size distribution and a mass distribution.

A injection guide 95 bent from the side wall of the freezing chamber 30 to an inner side is located above the through hole 92 formed in the tray 40. The injection guide 95 suppresses that a mist injected by the injection valve 12 passes through the through hole 92. It is preferable that the injection guide 95 can be detached. One end of the exhaust pipe 48 having the valve 50 is connected to the bottom of the freezing chamber 30. The other end of the exhaust pipe 48 is connected to the collect tray 52.

Figure 10:
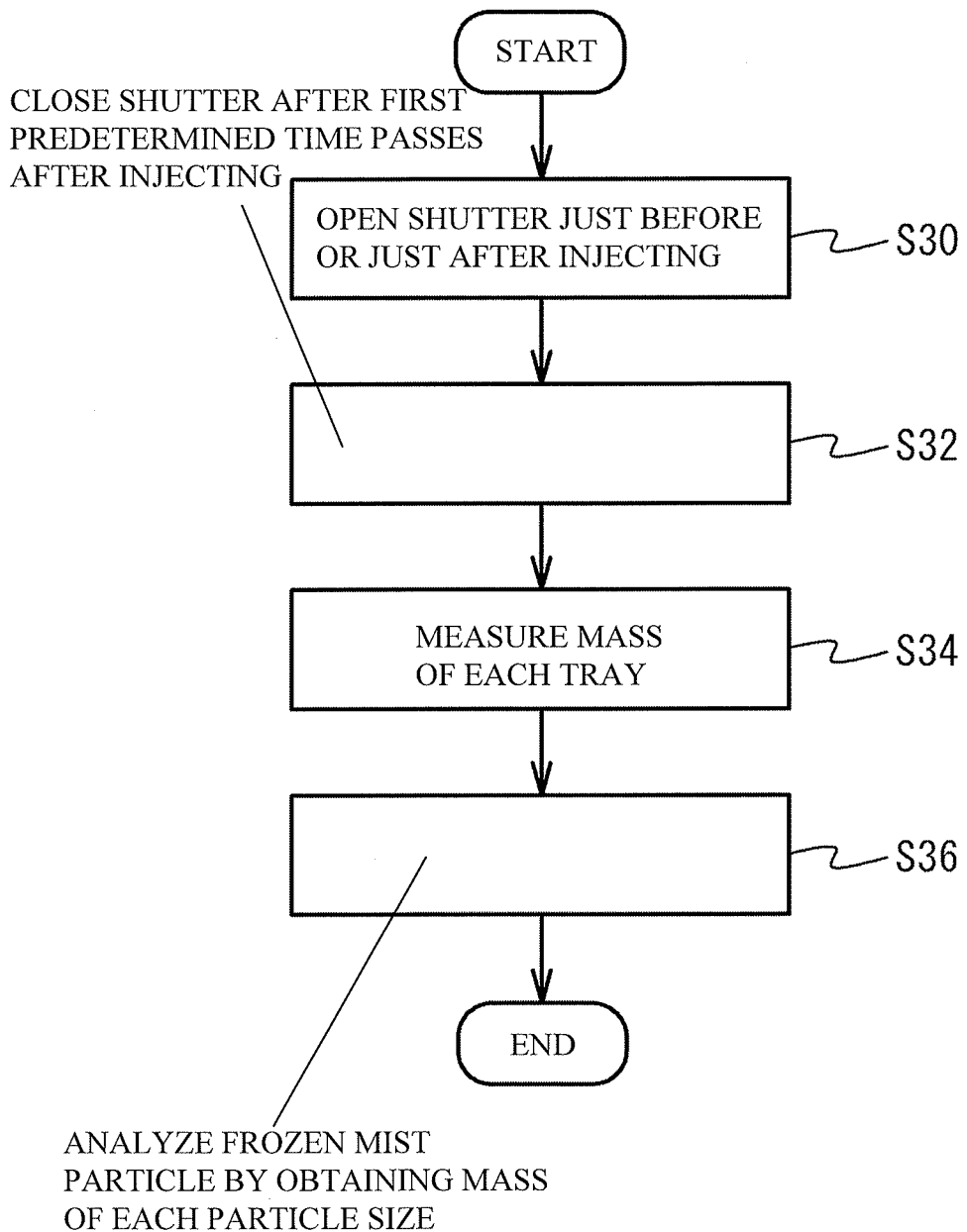
FIG. 10 illustrates an example of a flow chart indicating an analyzing method of the frozen mist particle.

A description is now given of a analyzing method of the frozen mist particle 42 held by each of the trays 40. FIG. 10 illustrates an example of a flow chart indicating the analyzing method of the frozen mist particle 42. With reference to FIG. 10, just before or just after the injecting of the injection valve 12, the control unit 80 drives the motor 64, rotates the shutter 60 by 90 degrees, and opens the shutter 60 (Step S30). Thus, the injection chamber 10 is communicated with the freezing chamber 30. A mist particle injected by the injection valve 12 is frozen in the freezing chamber 30 and becomes the frozen mist particle 42. The frozen mist particle 42 is held by each of the trays 40 according to the particle size.

Next, the control unit 80 drives the motor 64, rotates the shutter 60 by 90 degrees and closes the shutter 60 after a first predetermined time passes after the injecting (Step S32). The first predetermined time can be determined in view of a splitting time of a mist injected by the injection valve 12 as well as the embodiment 1.

Next, the control unit 80 measures a mass of each of the trays 40 after a predetermined time passes after the closing of the shutter 60 (Step S34). And, the control unit 80 obtains a mass of the frozen mist particle 42 with respect to the particle size from the increasing amount of the mass of each of the trays 40 after holding the frozen mist particle 42, and analyzes the frozen mist particle 42 (Step S36). For example, the number of particles is calculated from the mass of each particle size, and the particle size distribution or the mass distribution is obtained, After analyzing the frozen mist particle 42, the frozen mist particle 42 is collected by the following method. After analyzing the frozen mist particle 42, the shutter 60 is rotated by 90 degrees. The shutter 60 is opened. The injection chamber 10 is communicated with the freezing chamber 30. And, the valve 22 of the warm air flow pipe 20 connected to the upper portion of the injection chamber 10 is opened. A warm air is provided to the freezing chamber 30 from the injection chamber 10. The frozen mist particle 42 held by the tray 40 is unfrozen. The unfrozen frozen mist particle 42 is collected into the collect tray 52 via the exhaust pipe 48 of which the valve 50 is opened. And, after collecting the frozen mist particle 42, the shutter 60 is rotated by 90 degrees, and the shutter 60 is closed.

As in the case of the embodiment 3, the frozen mist particle 42 may be analyzed by providing a plurality of the trays 40 having a different mesh roughness and measuring the mass of the frozen mist particle 42 held by each of the trays 40. The mass of the frozen mist particle 42 can be obtained by particle size because each of the trays 40 holds the frozen mist particle 42 classified according to the particle size. The number of particles can be calculated from the mass of the frozen mist particle 42 of each particle size. And, the particle size distribution and the mass distribution can be obtained.

After analyzing the frozen mist particle 42, it is preferable that the frozen mist particle 42 is collected by unfreezing the frozen mist particle 42 held by the tray 40. Thus, it is possible to collect the frozen mist particle 42 speedily and easily, even if there are a plurality of the trays 40 holding the frozen mist particle 42.

In the embodiment 3, the case where the number of the trays 40 is eight is described. However, the structure is not limited to the case. A plurality of the trays 40 having a different mesh roughness may be provided. It is preferable that the tray 40 at the bottom has a plane shape. However, the tray 40 at the bottom may have a mesh of extremely small roughness.

In the embodiments 1 to 3, a plurality of mist particles are included in the mist injected by the injection valve 12. However, for example, a few mist particles such as one particle or two particles may be injected by the injection valve 12.

As mentioned above, preferable embodiments of the present invention are described in detail. The present invention is not limited to the specifically disclosed embodiments and variations but may include other embodiments and variations without departing from the scope of the present invention described in the CLAIMS.

DESCRIPTION OF LETTERS OR NUMERALS

10 Spray chamber
12 Spray valve
14a First camera
14b Second camera
16 Surface roughness measure unit
20 Warm air flow pipe
30 Freezing chamber
31 Side of freezing chamber
32 Coolant gas guide pipe
34 Pressure indicator
36 Flow rate regulate valve
38 Temperature sensor
40 Tray
42 Frozen mist particle
44 Light source
46 Concave portion
48 Exhaust pipe
52 Collect tray
54 Micro projection
56 Stirring fan
60 Shutter
62 Window
64 Motor
66 Wheel gear
68 Power supply
70 Invert unit
71 Drive device
72 Light source
74 High speed camera
76 Lens
80 Control unit
82 Shutter control unit
84 Coolant gas control unit
86 Analyze unit
88 Invert control unit
90 Concave portion
92 Through hole
94 Support rod
95 Mist guide
96 Burden sensor
98 Mass meter
100 Mist testing device
200 Mist testing device
300 Mist testing device
400 Mist testing device

The invention claimed is:

1. A mist testing device that tests a mist of a fuel injected by an injection valve used for an engine comprising:
    an injection chamber that splits and diffuses a mist of the fuel injected from the injection valve;
    a freezing chamber, of which temperature is kept low so that the split and diffused mist particle is frozen, that is communicated with the injection chamber;
    a shutter that switches a communication and non-communication between the injection chamber and the freezing chamber;
    a frozen-mist-hold unit that is provided within the freezing chamber and holds the frozen mist particle frozen in the freezing chamber; and
    an analyze unit that analyzes the frozen mist particle held by the frozen-mist-hold unit.

2. The mist testing device as claimed in claim 1 wherein the analyze unit analyzes the frozen mist particle by taking an image of the frozen mist particle held by the frozen-mist-hold unit.

3. The mist testing device as claimed in claim 2 wherein the mist testing device takes images of the frozen mist particle held by the frozen-mist-hold unit with two or more different focal lengths.

4. The mist testing device as claimed in claim 1, wherein the analyze unit analyzes the frozen mist particle by measuring a surface roughness of the frozen-mist-hold unit holding the frozen mist particle.

5. The mist testing device as claimed in claim 1 wherein:
    a plurality of the frozen-mist-hold units of which mesh has a different roughness are provided; and
    the analyze unit analyzes the frozen mist particle by measuring a mass of the frozen mist particle held by each of the plurality of the frozen-mist-hold units.

6. The mist testing device as claimed in claim 1 further comprising a shutter control unit that closes the shutter after the injecting of the mist by the injection valve is finished.

7. The mist testing device as claimed in claim 1 further comprising:
    a temperature measure unit that measures a temperature in the freezing chamber; and
    a coolant gas control unit that controls an amount of a coolant gas guided into the freezing chamber so that the temperature measured by the temperature measure unit is a predetermined temperature.

8. The mist testing device as claimed in claim 1 wherein:
    the freezing chamber has a circular cylinder shape; and
    a coolant gas guide pipe that introduces a coolant gas into the freezing chamber from an oblique direction with respect to a side wall of the freezing chamber having a circular cylinder is connected to the freezing chamber.

9. The mist testing device as claimed in claim 1 wherein the freezing chamber and the shutter are made of a member having a thermal conductivity lower than that of a member structuring the injection chamber.

10. The mist testing device as claimed in claim 1 wherein a stirring unit is provided in the freezing chamber.

11. The mist testing device as claimed in claim 1 further comprising a frozen mist collect unit that collects the frozen mist particle from the frozen-mist-hold unit after the analyzing by the analyze unit.

12. The mist testing device as claimed in claim 11 wherein the frozen mist collect unit inclines the frozen-mist-hold unit, drops a frozen mist particle held by the frozen-mist-hold unit from the frozen-mist-hold unit, and collects the frozen mist particle.

13. The mist testing device as claimed in claim 11 wherein the frozen mist collect unit collects the frozen mist particle by unfreezing a frozen mist particle held by the frozen-mist-hold unit.

14. The mist testing device as claimed in claim 11 wherein the frozen mist particle is collected to a collect tray via an exhaust path.

15. The mist testing device as claimed in claim 1 wherein:
    the frozen-mist-hold unit has micro projections provided at an interval of 0.1 μm or less; and
    the frozen mist particle is held on the micro projections.

16. The mist testing device as claimed in claim 1 further comprising an image unit that takes an image of a mist being injected by the injection valve.

\* \* \* \* \*